(12) United States Patent
Cajan et al.

(10) Patent No.: US 9,554,972 B2
(45) Date of Patent: Jan. 31, 2017

(54) HAIR TREATMENT COMPOSITION

(75) Inventors: Christine Cajan, Bad Ems (DE); Jutta Lehn, Darmstadt (DE)

(73) Assignee: KAO GERMANY GMBH, Darmstadt (DE)

( * ) Notice: Subject to any disclaimer, the term of this patent is extended or adjusted under 35 U.S.C. 154(b) by 2607 days.

(21) Appl. No.: 11/070,173

(22) Filed: Mar. 2, 2005

(65) Prior Publication Data

US 2005/0196372 A1 Sep. 8, 2005

(30) Foreign Application Priority Data

Mar. 5, 2004 (EP) .................................... 04005224

(51) Int. Cl.

| A61K 8/06 | (2006.01) |
|---|---|
| A61K 8/41 | (2006.01) |
| A61K 8/86 | (2006.01) |
| A61K 8/891 | (2006.01) |
| A61K 8/92 | (2006.01) |
| A61Q 5/06 | (2006.01) |
| A61Q 5/12 | (2006.01) |

(52) U.S. Cl.
CPC ............... *A61K 8/068* (2013.01); *A61K 8/416* (2013.01); *A61K 8/86* (2013.01); *A61K 8/891* (2013.01); *A61K 8/92* (2013.01); *A61Q 5/06* (2013.01); *A61Q 5/12* (2013.01)

(58) Field of Classification Search
USPC .............. 424/401, 70.1, 70.11, 70.12, 70.19, 424/70.22, 70.23, 70.24, 70.74
See application file for complete search history.

(56) References Cited

U.S. PATENT DOCUMENTS

| 3,101,301 | A | * | 8/1963 | Siegal et al. ............... 424/70.19 |
|---|---|---|---|---|
| 3,927,199 | A | | 12/1975 | Micchelli et al. |
| 4,218,334 | A | * | 8/1980 | Lundmark ...................... 516/75 |
| 4,240,450 | A | | 12/1980 | Grollier et al. |
| 4,761,273 | A | | 8/1988 | Grollier et al. |
| 4,970,220 | A | * | 11/1990 | Chaussee ...................... 514/358 |
| 5,133,885 | A | * | 7/1992 | Contor et al. ................ 510/521 |
| 5,256,403 | A | * | 10/1993 | Gaskin ............................ 424/59 |
| 5,441,671 | A | * | 8/1995 | Cheney et al. ............... 510/156 |
| 6,126,954 | A | * | 10/2000 | Tsaur ............................ 424/401 |
| 6,241,976 | B1 | * | 6/2001 | Esser et al. ...................... 424/65 |
| 6,274,540 | B1 | * | 8/2001 | Scheibel et al. ............. 510/352 |
| 6,316,030 | B1 | * | 11/2001 | Kropf et al. .................. 424/489 |
| 6,348,439 | B1 | * | 2/2002 | Rousso et al. ................ 510/125 |
| 6,419,938 | B1 | * | 7/2002 | Riedel et al. ................. 424/401 |
| 6,468,514 | B2 | * | 10/2002 | Schmucker et al. ....... 424/70.19 |
| 2002/0058052 | A1 | * | 5/2002 | Hasebe et al. ............... 424/401 |
| 2003/0108501 | A1 | * | 6/2003 | Hofrichter et al. .......... 424/70.1 |
| 2005/0215443 | A1 | * | 9/2005 | Littau et al. .................. 510/130 |

FOREIGN PATENT DOCUMENTS

| DE | 2521960 | A1 | | 4/1976 | |
|---|---|---|---|---|---|
| DE | 2811010 | A1 | | 9/1978 | |
| DE | 3044738 | A1 | | 6/1981 | |
| DE | 3217059 | A1 | | 11/1982 | |
| DE | 19751550 | A1 | * | 7/1999 | |
| DE | 10200341 | A1 | | 7/2003 | |
| EP | 0337354 | A1 | | 10/1989 | |
| EP | 0524612 | A2 | | 1/1993 | |
| EP | 0640643 | A2 | | 3/1995 | |
| EP | 1097701 | A1 | | 5/2001 | |
| EP | WO 03/094872 | | * | 11/2003 | ............. A61K 7/075 |
| GB | 1513672 | | | 6/1978 | |
| WO | 9268899 | A1 | | 4/1992 | |
| WO | 9310748 | A1 | | 6/1993 | |
| WO | 9416677 | A1 | | 8/1994 | |
| WO | WO9913839 | A1 | * | 3/1999 | |
| WO | 0000171 | A1 | | 1/2000 | |
| WO | 02096381 | A1 | | 12/2002 | |
| WO | WO 02096381 | A1 | * | 12/2002 | |
| WO | 03022235 | A2 | | 3/2003 | |

OTHER PUBLICATIONS

Schubel and Ilgenfritz, 1997. Influence of polyethylene glycols on the percolation behavior of anionic and nonionic water-in-oil microemulsions. Langmuir, vol. 13(16):4246-4250.*
Patani and LaVoie, 1996. Bioisosterism: A rational approach to drug design. Chem. Rev., vol. 96(8):3147-3176.*
Schubel and Ilgenfritz, 1997. Influence of polyethylene glycols on the percolation behavior of anionic and nonionic water-in-oil microemulsions. Langmuir, vol. 13(16):4246-4250; as provided in the Apr. 14, 2009 office action.*
Johannsen 1992. New possibilities to formulate cosmetic and pharmaceutical emulsions without fatty alcohols. Comunicaciones presentadas a la Jornadas del Comite Espanol de la Detergencia, vol. 23:53-65.*
Patani and LaVoie, 1996. Bioisosterism: A rational approach to drug design. Chem. Rev., vol. 96(8):3147-3176; as provided in the Apr. 14, 2009 office action.*
Surfactants for Industrial Applications 2004, http://www.hui.edu.vn/khoahoa/data/files/SACH%20THAM%20KHAO%20CHDBM/Surfactants_for_Industrial_Applications.pdf.*
Azeem et al. Rec. Patents on Drug Deliv. & Formulation, 2008, 2, 275-289.*

* cited by examiner

*Primary Examiner* — Jianfeng Song
(74) *Attorney, Agent, or Firm* — Norris McLaughlin & Marcus PA

(57) ABSTRACT

A hair treatment composition is in the form of an emulsion, preferably of a micro emulsion, which improves hair quality in terms of softness, shine and touch feeling. Emulsion type of hair treatment composition is characterized in that it includes in a cosmetically acceptable aqueous medium
   a—one or more surfactants as emulsifier,
   b—one or more natural and/or mineral oil,
   c—one or more silicone oil, and
   d—at least one polyethyleneglycol with a molecular weight of more than 10,000.

18 Claims, No Drawings

HAIR TREATMENT COMPOSITION

The present invention concerns a hair treatment composition in the form of an emulsion, preferably of a micro emulsion, which improves hair quality.

Compositions for the treatment of human hair have been known for some time, they generally comprise various conditioning substances. Such compositions are customarily used as aqueous dispersions or emulsions, micro-emulsions or gels. An overview of the known hair treatment preparations and the composition thereof can be found, e.g., in the monography of K. Schrader, "Grundlagen und Rezepturen der Kosmetika", $2^{nd}$ Ed. (1989), pages 722 to 736, 754 to 760.

Post-treatment compositions, also including styling preparations, are customarily applied subsequently to a hair treatment, in particular after washing with a shampoo composition or eventually after conditioning hair either with a rinse off hair conditioner also know as treatment or rinse preparations or after a leave in as well conditioner composition or also a coloration or permanent waving treatment terminating with a final shampoo or rinse treatment.

So-called hair waxes have also become known, which, as the name implies, consist of natural or synthetic products, In spite of their initial superficial conditioning performance, those products have been proven to weigh down hair and result in after a short period of time loss of volume. Furthermore, hair feel is judged to be, by hair specialists as well by group of consumer often using the product, is very artificial and not cosmetic at all in terms of hair softness, finger through and/or flexibility. The user of the product group especially complains on oily and/or artificially covered feeling of hair after application of the products.

Additionally, the wax type of preparations has one important practical usage problem, which is removability from product packaging as they are usually packed into a jar type of containers. A solution to such kind of problem has been suggested in a German Patent Application from the same applicant, which is published under number DE 102 00 341 A1, as lowering melting point of the formulation, so that it melts quickly when touching the product with fingers. This may overcome the practical problem of removability, but will not help at all in solving aforementioned cosmetic problems.

The objective of the present invention is therefore, making a composition available, which does not show above mentioned cosmetic problems.

Those problems are solved by using a hair treatment composition on aqueous basis in the form of an emulsion, preferably a micro emulsion comprising
- a—one or more emulsifying surfactants,
- b—one or more natural and/or mineral oil,
- c—at least one silicone oil, and
- d—at least one polyethylene glycol with a molecular weight of more than 10,000.

The emulsion composition according to the invention is preferably a micro emulsion, which is either non-transparent or semi-transparent and can as well transparent appearance.

Compositions according to the invention improve hair properties in terms of especially soft texture, gloss, elasticity, flexibility, bounce and in particular improved formability and thereby better compliance. Gloss, softness and natural feeling when touching hair are found to be particularly important properties of the hair treatment compositions of the present invention.

The surfactants suitable for the compositions according to the invention are first of all those nonionic surfactants. Hair treatment compoisitions according to the invention comprises one or more nonionic surfactants. Preferred nonionic surfactants are ethoxylated fatty alcohols according to the following formula:

where $R_1$ is a saturated or unsaturated, linear or branched alkyl chain with 12 to 22 C atoms and n is a number between 2 and 50 prefrably 2 to 40, more preferably 2 to 30. In one of the prefreed embodiments of the invention, the hair treatment compositions comprise a mixture of two nonionic fatty alcohol ethoxylates, one has between 2 to 10 ethoxylate units and the other is more than 10. Those surfactants are known by the generic terms for example "Laureth", "Myristeth", "Oleth", "Ceteth", "Deceth", "Steareth" and "Ceteareth" according to the CTFA nomenclature, including addition of the number of ethylene oxide molecules. e.g. "Ceteareth-20", Steareth-2, Further nonionic surfactants suitable as emulsifiers in hair treatment compositions according to the invention are those polyethylene glycol ethers of monogylcerides according to the general formula

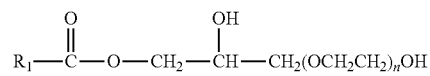

$R_1$ and n are same as above. Examples to those types of nonionic surfactants are PEG-7-glyceryl cocoate known with the trade name Cetiol HE from Cognis, PEG-8-glyceryl laurate know with the trade name Glycerox L8 from Croda Chemicals, PEG-10 glyceryl oleate, PEG-15 glycerryl isostearate, PEG-5 glycerryl stearate, PEG-15 gylceryl ricinoleate, etc.

Further nonionic surfactants suitable for treatment compositions according to the invention are alkyl polyglucosides of the general formula

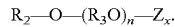

wherein $R_2$ is an alkyl group with 8 to 18 carbon atoms, $R_3$ is an ethylene or propylene group, Z is a saccharide group with 5 to 6 carbon atoms, n is a number from 0 to 10 and x is a number between 1 and 5.

Nonionic surfactant components are, for example, long-chain fatty acid mono- and dialkanolamides, such as coco fatty acid monoethanolamide and myristic fatty acid monoethanolamide, which can also be used as emulsifiers according to the invention.

Additionally useful nonionic surfactants are the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®", as well as fatty alcohol ethoxylates.

Still further suitable nonionic surfactants as emulsifiers are aminoeoxides. Such aminoeoxides are known especially because of their use in cleansing compositions, for example $C_{12}$-$C_{18}$-alkyl dimethyl aminoeoxides such as lauryl dimethyl aminoeoxide, $C_{12}$-$C_{18}$-alkyl amidopropyl or -ethyl amineoxides, $C_{12}$-$C_{18}$-alkyl di(hydroxyethyl) or (hydroxypropyl) aminoeoxides, or also aminoeoxides with ethyleneoxide and/or propyleneoxide groups in the alkyl chain, Those are on the market, for example, under the trade names "Ammonyx®", "Aromox®" or "Genaminox®".

Concentration of nonionic surfactants in total independent from presence of number of surfactants as emulsifiers is between 0.5% and 35%, preferably 1% and 30% and most preferably 5 and 25% by weight calculated to the total composition.

Hair treatment composition of the present invention can comprise further anionic surfactants as emulsifiers, preferred in a mixture with one or more nonionic surfactants. The mixing ratio of nonionic and anionic surfactants is in the range of 10:1 to 1:3. preferably 5:1 to 1:2. most preferably 2:1 to 1:1.

Concentration of anionic surfactants in the hair treatment compositions of the present invention can vary between 0.5% and 35%, preferably 1% and 30% and most preferably 1% and 25% by weight calculated to the total composition.

Suitable anionic surfactants are in general those known from cleansing compositions. In particular, fatty acids or ethoxylated fatty acids phosphate esters are suitable in the treatment compositions of the present invention according to general formula

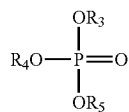

where R3, R4 and R5 are same or different, saturated or unsaturated, linear or branched alkyl chain with 10 to 22 C atoms or

where R3, R4 and R5 are same as above and n is 1 to 10.

Non-limiting examples to such surfactants are trilaureth-4-phosphate known with the trade name Hostaphat from Clariant, trideceth-6-phosphate, trideceth-10-phosphate and tristeareth-4-phosphate. Trilaureth-4-phosphate is the most preferred one among them.

Further anionic surfactants of the sulfate, sulfonate, carboxylate types are as well suitable as emulsifiers in the hair treatment composition of the present invention. Those are the ones very commonly used in cosmetic cleansing preparations, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof.

Additional anionic surfactants useful within the scope of the invention are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof of the formula

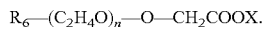

wherein $R_6$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted, as well as alkyl amido polyether carboxylic acids of the general formula

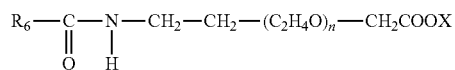

wherein $R_6$ and X have the above meanings, and n is in particular a number from 1 to 10, preferably 2.5 to 5.

Such products have been known for some time and are on the market, for example, under the trade name "AKYPO®" and "AKYPO-SOFT®".

Also useful are $C_8$-$C_{20}$-acyl isethionates, alone or in mixture with other anionic surfactants, as well as sulfofatty acids and the esters thereof.

It is also possible to use mixtures of several anionic surfactants in mixture within the scope of the invention.

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N-$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

As further surfactant component, the compositions according to the invention can also contain amphoteric or zwitterionic surfactants as emulsifiers.

Useful as such are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also proven suitable.

In detail, it is possible to use betaines of the structure

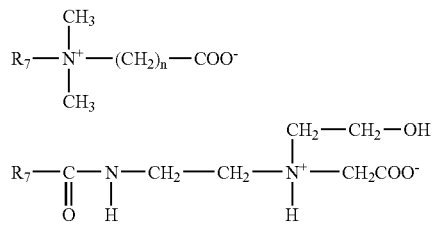

wherein $R_7$ is a $C_8$-$C_{18}$-alkyl group and n is 1 to 3; sulfobetaines of the structure

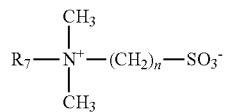

wherein $R_7$ and n are same as above;
and amidoalkyl betaines of the structure

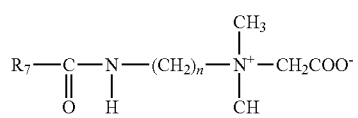

wherein $R_7$ and n are same as above.

Hair treatment composition of the present invention comprises one or more oil and/or mineral oil at a concentration of 1% to 35%, preferably 1 to 30% and most preferably 5 to 25% by weight calculated to total composition, Suitable natural oils are such as avocado oil, coconut oil, palm oil, sesame oil, peanut oil, whale oil, sunflower oil, almond oil, peach kernel oil, wheat germ oil, macadamia nut oil, night primrose oil, jojoba oil, castor oil, or also olive oil, soya oil, and the derivatives thereof. Mineral oils such as paraffin oil and petrolatum are suitably contained within the scope of the present invention, It should as well be noted that hair treatment compositions can contain mixture of one or more natural oils and mineral oil.

Further suitable hydrophobic oil components are in particular fatty alcohol fatty acid esters such as isopropyl myristate, palmitate, stearate and isostearate, oleyl oleate, isocetyl stearate, hexyl laurate, dibutyl adipate, dioctyl adipate, myristyl myristate, oleyl erucate, polyethylene glycol and polyglyceryl fatty acid esters, cetyl palmitate, etc.

At least one silicone oil is the fourth essential part of the hair treatment compositions within the scope of the present inventions. Those are contained in mixture with natural and/or mineral oils in a weight ratio 20:1 to 1:1, preferably 15:1 to 1:1 and more preferably 10:1 to 1:1 (ratio of sum of natural and/or mineral oils to silicone oil). Preferred are the non-volatile silicone oils.

Preferred ones are known with their INCI name as dimethicone, dimethiconol and cyclomethicone, Commercially, they are available from various companies for example Dow Corning with the known DC series, Wacker Chemie and Toray silicones. All commercially available non volatile silicones are suitable in the compositions of the present invention. Examples to those are DC 200 series, DC1401, DC 1403, DC 1501 and DC 1503. Volatile silicone oils can as well be contained in the hair treatment compositions in mixture with nonvolatile silicone oils within the scope of the present invcention with the consition that their content should not exceed ¼, preferably ⅒ of the nonvolatile silicone oil content of the composition.

Cationic silicones know with INCI name as amodimethicone can as well be contained in the compositions of the present invention. Commercially it is available under the trade name DC 929 in emulsified form in mixture with a nonionic surfactant and a cationic surfactant.

Concentration of silicone oils in hair treatment compositions of the present invention is in the range between 0.1% and 10%, preferably 0.1% and 7.5% and most preferably 0.1 and 5% by weight calculated to total composition.

Hair treatment compositions of the present invention can be in the form of either leave in or rinse off emulsions, especially micro emulsions, used on hair, preferably after shampooing. Leave-in application of the compositions of the present invention is preferred. In the case of a leave in application, the treatment composition of the present invention can as well be used on dry hair without washing and/or shampooing hair for refreshing the hair properties, especially softness and shine.

Hair treatment compositions according to the present invention do not contain any fatty and wax components. In the especially preferred embodiment the compositions of the present invention are free of any fatty alcohol.

The fourth essential component in the treatment compositions of the present invention is those high molecular weight polyethyleneglycols with a molecular weight of above 10.000. Further examples are such as PEG-14M, PEG-20M, PEG-23M, PEG-25M, PEG-45M, PEG-90M, PEG-115M, PEG-160M, etc.

Concentration of the high molecular weight polyethyleneglycols is in the range of 0.05% to 2.5%, preferably 0.1% to 1.5% and most preferably between 0.1 to 1.0% by weight calculated to total composition.

Cationic surfactants are useful in the compositions of the present invention as emulsifiers and as conditioning agents at the same time represented with the general formula below:

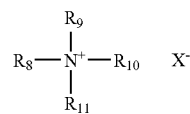

where $R_8$ is a saturated or unsaturated, branched or non-branched alkyl chain with 8-22 C atoms or

where $R_{12}$ is saturated or unsaturated, branched or non-branched alkyl chain with 7-21 C atoms and n has typical value of 0-4 or

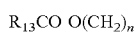

where $R_{13}$ is saturated or unsaturated, branched or non-branched alkyl chain with 7-21 C atoms and n has typical value of 0-4. and $R_9$ is a hydrogen, lower alkyl chain with 1 to 4 carbon atoms, saturated or unsaturated, branched or non-branched alkyl chain with 8-22 C atoms or

where $R_{12}$ is saturated or unsaturated, branched or non-branched alkyl chain with 7-21 C atoms and n has typical value of 0-4 or

where $R_{13}$ is saturated or unsaturated, branched or non-branched alkyl chain with 7-21 C atoms and n has typical value of 0-4. and $R_{10}$ and $R_{11}$ are independent from each other H or lower alkyl chain with 1 to 4 carbon atoms, and X is chloride, bromide or methosulfate.

It should be noted that quaternary ammonium compounds with single alkyl chain are as well emulsifiers. This should certainly not mean that, they are excluded to be used as conditioning ingredients. With the above it is especially stated that the single alkyl chain cationic surfactants have emulsifying ability as well. The others, such as di alkyl dimonium chloride, is more preferred as conditioner as will be explained below. Suitable cationic surfactants and or conditioning agents are, for example, long-chain quaternary ammonium compounds which can be used alone or in admixture with one another, such as cetyl trimethyl ammonium chloride, myristoyl trimethyl ammonium chloride, trimethyl cetyl ammonium bromide, stearyl trimethyl ammonium chloride, dimethyl stearyl ammonium chloride, dimethyl dihydrogenated tallow ammonium chloride, stear trimonium chloride, dipalmitoyl dimonium chloride, distearyl dimethyl ammonium chloride, stearamidopropyl trimonuim chloride and dioleoylethyl dimethyl ammonium methosulfate, etc.

From the above quaternary ammonium compounds disclosed with the general formula, especially preferred as hair conditioning agents are those compounds known per se and are on the market, for example, under the trade names "Schercoquat®", "Dehyquart® F30" and "Tetranyl®". Use of these compounds, the so-called "esterquats", in hair care compositions is described, for example, in WO-A 93/107 48, WO-A 92/068 99 and WO-A 94/166 77, wherein, however, there is no reference made to the combinations according to the present invention and the advantageous properties thereof.

Again from the above quaternary ammonium compounds disclosed with the general formula, especially preferred as conditioning ingredient are these compounds are known per se and on the market, for example, under the trade name "INCROQUAT® HO" or "OCS". Those compounds are known with a general ingredient category under "amidoquat" in the cosmetic industry.

A further preferred component used in the emulsions or micro emulsions according to the present invention are polyols such as propylene glycol, glycerol, sorbitol, propanediol and butanediol. preferably in an amount from 1% to 50%, preferably 1% to 40% and more preferably 5% to 30% and most preferably 5% to 25% by weight. in particular about 10% to about 25% by weight, calculated to the total emulsion.

Composition of the present invention may comprise cationic polymers as conditioning agents. Those are cationic cellulose type polymers know as Polymer JR type from Amerchol such as Polyquaternium 10 or cationic guar gum known with trade name Jaguar from Rhone-Poulenc and chemically for example Guar hydroxypropyl trimonium chloride. Furthermore. chitosan and chitin can also be included in the compositions as cationic natural polymers.

Furthermore, those cationic polymers known with their CTFA category name Polyquaternium may as well be added into the compositions of the present invention. Typical examples of those are Polyquaternium 6, Polyquaternium 7, Polyquaternium 10, Polyquaternium 11, Polyquaternium 16, Polyquaternium 22 and Polyquaternium 28, Polyquaternium 30, Polyquaternium 37, Polyquaternium 36, Polyquaternium 46.

As well those polymers known with their CTFA category name Quaternium can as well be suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-81, Quaternium-82, Quaternium-83 and Quaternium-84.

In this context, reference is also made to the cationic polymers disclosed in DE 25 21 960, 28 11 010, 30 44 738 and 32 17 059, as well as to the products described in EP-A 337 354 on pages 3 to 7, It is also possible to use mixtures of various cationic polymers.

The cationic polymers also include the quaternized products of graft polymers from organopolysiloxanes and polyethyl oxazolines described in EP-A 524 612 and EP-A 640 643.

The compositions according to the invention may also comprise further agents, such as protein hydrolyzates and polypeptides, e.g. keratin hydrolyzates, collagen hydrolyzates of the type "Nutrilan®" or elastin hydrolyzates, as well as, in particular vegetable, optionally cationized protein hydrolyzates, for example "Gluadin®".

Additional natural plant extracts can as well form part of the compositions of the present invention. Those are incorporated usually in an amount of about 0.01% to about 5%, preferably 0.05% to 3.5%, in particular 0.1% to 2% by weight, calculated as dry residue thereof to the total composition. Suitable aqueous (e.g. steam-distilled) alcoholic or hydro-alcoholic plant extracts known per se are in particular extracts from leaves, fruits, blossoms, roots, rinds or stems of aloe, pineapple, artichoke, arnica, avocado, valerian, bamboo, henbane, birch, stinging nettle, echinacea, ivy, wild angelica, gentian, ferns, pine needles, silver weed, ginseng, broom, oat, rose hip, hamamelis, hay flowers, elderberry, hop, coltsfoot, currants, chamomile, carrots, chestnuts, clover, burr root, coconut, cornflower, lime blossom, lily of the valley, marine algae, balm, mistletoe, passion flower, ratanhia, marigold, rosemary, horse chestnut, pink hawthorn, sage, horsetail, yarrow, primrose, nettle, thyme, walnut, wine leaves, white hawthorn, etc.

Suitable trade products are, for example, the various "Extrapon®" products, "Herbasol®", "Sedaplant®" and "Hexaplant®". Extracts and the preparation thereof are also described in "Hagers Handbuch der pharmazeutischen Praxis". $4^{th}$ Ed.

The hair treatment compositions compositions may contain one or more organic solvents within the scope of the invention, such as ethanol, propanol, isopropanol, benzyl alcohol, benzyloxyethanol, alkylene carbonates such as ethylene carbonate and propylene carbonate, phenoxyethanol, butanol, isobutanol, cyclohexane, cyclohexanol, hexyleneglycol, ethylenecarbonate, ethyleneglycol monoethylether, ethylene glycol monobutyl ether, ethylene glycol monophenyl ether, 1-phenylethylalcohol, 2-phenylethylalcohol, o-methoxyphenol. Concentration of organic solvents in the composition should not exceed 10%, preferably 7.5 and more preferably 5% by weight.

Compositions of the present invention may contain UV filters either for stabilization of the product colour or for protection of hair from environmental influences such as loss of elasticity, loss of hair colour (bleaching effect of sun light). The UV-absorbing substance is preferably selected from the following compounds: 4-Aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxycinnamic acid and the esters and salts thereof, salicylic acid and the esters and salts thereof, 2,4-dihydroxybenzophenone, 2,2', 4,4'-tetrahydroxybenzophenone, 2-hydroxy-4-methoxybenzophenone and its 5-sulfonic acid or the sodium salt thereof, 2,2'-dihydroxy-4,4'-dimethoxybenzophenone, 2-hydroxy-5-chlorobenzophenone, 2,2'-dihydroxy-4-methoxybenzophenone, 2,2'-dihydroxy-4,4'-dimethoxy-5,5'-disulfobenzophenone or the sodium salt thereof, 2-hydroxy-4-octyloxybenzophenone, 2-hydroxy-4-methoxy-4'-methylbenzophenone, 3-benzyl-idenecampher, 3-(4'-sulfo)-benzyl-idenebornane-2-one and the salts thereof and/or 3-(4'-methyl benzylidene)-DL-campher.

The preferred amount of the UV-absorber ranges from about 0.01% to 2.5%, more preferably from 0.05% to 1% by weight, calculated to the total composition. Attention should be paid to the emulsion stability and appearance especially when using UV filter as salts, e.g. anionic UV filter salts. A general well known rule among the cosmetic chemists is that stability and appearance of emulsions can greatly be affected by addition of salts.

The compositions of the present invention can comprise hair-restructuring agents. The hair restructuring agents preferred are especially the ones disclosed in the German patent DE 197 51 550 C2.

One of the known hair restructuring agents is ceramide type of compound with the general formula

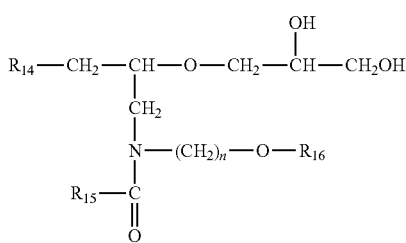

where $R^{14}$ and $R^{15}$ are independent from each other alkyl- or, alkenyl group mit 10 to 22 carbon atoms, $R^{16}$ is methyl, ethyl, n-propyl or isopropyl group and n is a number between 1 to 6, preferably 2 or 3.

Other preferred hair restructuring agents are fatty acids with 10 to 24 carbon atoms and especially with 16 to 24 carbon atoms.

Sterols, especially the phytosterols, are as well preferred hair restructuring agents as disclosed in the above mentioned german patent. Especially preferred ones are of plant origin for example ergosterol, sitosterol, stigmasterol, fucosterol, brassicasterol, fungisterol, campesterol, zymosterol, ascosterol, cerevisterol, episterol, faecosterol, spinasterol. Among those phytosterols, the ones found in "Avocadin" which is the unsaponified fraction of the avocado oil is more preferred.

The concentration of ceramide in the compositions of the present invention can be in the range of 0.01% to 2% and especially 0.01% to 1% by weight calculated to the total weight of the composition. The fatty acids may be contained at a level of 0.01 to 2.5% and epecially 0.01 to 1% by weight calculated to the total weight of the composition. Phytosterol concentration of the conditioners is less than 1% and preferably less than 0.5% by weight calculated to the total weight of the composition. It should be noted without limiting the use of those ingredients the effect of those hair restructuring ingredients is especially elevated when all three of above mentioned ingredients are used in combination with penetration enhancers.

The hair treatment composition can contain complexing agents, solubilizers, preservatives, pH-regulants, the extent they are not already contained in the original surfactant mixtures, fragrances, thickening agents, and moisturizers.

The pH of the compositions according to the invention is in the range of 5 to 8. For adjusting the pH of the said compositions, following ingredients can be used: Organic acids such as citric acid, tartaric acid, fumaric acid, levulinic acid, butyric acid and hydroxy butyric acids, valeric acid, oxalic acid, succinic acid, mandelic acid, glycolic acid, glucuronic acid, propionic acid, salicylic acid or acetic acid or inorganic acids such as hydrochloric acid, phosphoric acid, sulphuric acid, nitric acid.

The viscosity of the compositions is above 100,000 mPa·s measured with a Brookfield viscosimeter at 20° C. from a Helipath Spindle Set with a spindle F at 10 rpm. Viscosity values are preferably above 250,000 and more preferably above 400,000.

The styling polymer or polymers is/are selected from the anionic, non-ionic, cationic and/or amphoteric or zwitterionic ones can as well be contained in the hair treatment compositions according to the present invention.

Non-ionic polymers are selected from the ones soluble in water and/or alcohol and/or in alcohol water mixtures, at any ratio. Under the definition of soluble in alcohol and alcohol water mixture, it should be understood that the polymer is soluble in lower alcohols such as ethanol, n-propanol or isopropanol and in their mixtures with water, at any ratio.

Suitable non-ionic polymer is first of all vinylpyrrolidon polymers either homopolymers or copolymers with, especially, vinylacetate. Those are known with the trade name "Luviskol" as homopolymers Luviskol K 30, K 60 or K 90 as well copolymers Luviskol VA 55, VA 64 from BASF AG.

Further non-ionic polymer suitable for compositions of the present invention is vinylpyrrolidone/vinylacetae/vinylpropionate copolymer known with the trade name Luviskol VAP 343 as well from BASF.

Natural non-ionic polymers are as well suitable for the composition of the present invention. Those are such as cellulose, chitosan, guar gum, neutralised shellac and their derivatives.

Amphoteric or zwitterionic polymers may be contained in composition of the present invention. Examples are copolimerisate of n-octylacrylamide, acrylic or metahcrylic acid and tert.-butylaminoethylmethacrylate known with its trade name Amphomer, copolymer of methacryloylethylbetaine and alkyl methacrylate known as Yukaformer, terpolymer of metahcrylic or acrylic acid and itaconoic acid and a basic monomer of mono or dialkylaminoalkyl acrylate or methacrylate or acrylate of methacrylamide known with the trade name Aquaflex SF 40.

As amphoteric polymers which can be used alone or in mixture with at least one additional cationic and/or nonionic polymer, reference is here made in particular to copolymers of N-octyl acrylamide, (meth)acrylic acid and tert.-butyl aminoethyl methacrylate of the type "Amphomer®"; copolymers from methacryloyl ethyl betaine and alkyl methacrylates of the type "Yukaformer®", e.g. the butyl methacrylate copolymer "Yukaformer® Am75"; copolymers from monomers containing carboxyl groups and sulfonic groups, e.g. (meth)acrylic acid and itaconic acid, with monomers such as mono- or dialkyl aminoalkyl(meth)acrylates or mono- or dialkyl aminoalkyl(meth)acrylamides containing basic groups, in particular amino groups; copolymers from N-octyl acrylamide, methyl methacrylate, hydroxypropyl methacrylate, N-tert.-butyl aminoethyl methacrylate and acrylic acid, as well as the copolymers known from U.S. Pat. No. 3,927,199.

Anionic polymers may as well be contained in compositions of the present invention. Suitable ones are vinyl alkyl ether, in particular methyl vinyl ether/maleic acid copolymers, obtained by hydrolysis of vinyl ether/maleic anhydride copolymers, distributed under the trade name "Gantrez® AN or ES". These polymers may also be partly esterified, as for example, "Gantrez® ES 225" or "ES 435", the ethyl ester of an ethyl vinyl ether/maleic acid copolymer, or the butyl or isobutyl ester thereof.

Further useful anionic polymers are in particular vinyl acetate/crotonic acid or vinyl acetate/vinyl neodecanoate/crotonic acid copolymers of the type "Resyn®"; sodium acrylate/vinyl alcohol copolymers of the type "Hydagen® F", sodium polystyrene sulfonate, e.g. "Flexan® 130"; ethyl acrylate/acrylic acid/N-tert.-butyl acrylamide copolymers of the type "Ultrahold®"; vinyl pyrrolidone/vinyl acetate/itaconic acid copolymers, acrylic acid/acrylamide copolymers or the sodium salts thereof of the type "Reten®"; etc.

Concentration of polymers of anionic, cationic, non-ionic and/or amphoteric or zwitterionic character is in the range of 0.05-10%, preferably 0.05-7.5% and most preferably 0.05-5% by weight, calculated to the total composition.

The following examples are nonlimiting and to illustrate the invention.

EXAMPLE 1

According to the Invention

| Phase A) | |
| --- | --- |
| Ceteareth-20 | 20.00% |
| PEG-7 Glyceryl cocoate | 10.00% |
| Mineral oil | 15.00% |
| Dimethicone | 2.00% |
| Phase B) | |
| Water | add 100% |
| Glycerin | 15.00% |
| DMDM hydantoin | 0.20% |
| Propylene glycol | 5.00% |
| PEG-45M | 0.40% |
| Phase C) | |
| Parfum | 0.30% |

Phase A and Phase B are heated up to 80° C. and subsequently Phase B is mixed into Phase A under continuous agitation. After cooling down to 60° C. Phase C is added and the mixture is cooled down to room temperature. The preparation so obtained has a viscosity of 1,200,000 mPa·s measured as given in the description. pH of the composition measured at ambient temperature is around 6.0.

EXAMPLE 2

Not According to the Invention

| Phase A | |
| --- | --- |
| Ceteareth-20 | 20.00% |
| PEG-7 glyceryl cocoate | 10.00% |
| Mineral oil | 17.00% |
| Phase B | |
| Aqua | add 100% |
| Glycerin | 15.00% |
| DMDM hydantoin | 0.20% |
| Propylene glycol | 5.00% |
| PEG-45M | 0.40% |
| Phase C | |
| Parfum | 0.30% |

The composition is prepared in the same way as in the example 1. The preparation so obtained has a viscosity of 1,400,000 mPa·s measured as given in the description. pH of the composition measured at ambient temperature is around 6.0.

The examples 1 and 2 are compared in a half side comparison test. For this purpose 10 volunteers with shoulder length hair are selected. After washing hair of the volunteers with a commercially available shampoo under the brand name Goldwell Definition and drying with a hair dryer, equal amounts (approximately 0.75 g per half side) of the examples 1 and 2 are applied each half side. Hair properties are evaluated by at least 3 expert hairdressers.

From the evaluation results it is obvious that the side treated with the example 1 showed always significantly better shine and softness. The other side is evaluated to have significantly less shine than the side treated with example 1. In addition the stylability and volume of the hair is judged to be better in 60% of the case for inventive preparation and in the remaining cases no difference is found.

EXAMPLE 3

According to the Invention

| Phase A) | |
| --- | --- |
| Isoceteth-20 | 10.00% |
| Ceteareth-20 | 10.00% |
| Steareth-2 | 6.00% |
| Mineral Oil | 11.00% |
| Dimethicone | 2.00% |
| Phase B) | |
| Aqua | add 100% |
| Propylene Glycol | 5.00% |
| PEG-45M | 0.40% |
| DMDM Hydantoin | 0.20% |
| Glycerin | 7.00% |
| Phase C) | |
| Parfum | 0.30% |

The composition is prepared in the same way as in the example 1. The preparation so obtained has a viscosity of 1,100,000 mPa·s measured as given in the description.

The composition of example 3 is compared to a composition not containing any PEG 45M and dimethicone otherwise quantitatively same as the composition 3 in a half side comparison test. For this purpose 10 volunteers with shoulder length hair are selected. After washing hair of the volunteers with a commercially available shampoo under the brand name Goldwell Definition and drying with a hair dryer. Equal amounts of preparations (0.75 g per half side of inventive and non inventive compositions) are applied each half side. Hair properties are evaluated by at least 3 expert hairdressers.

From the evaluation results, it is obvious that the side treated with the example 3 (inventive composition) showed always significantly better softness and better feeling when touching hair and especially high brilliance (shine). The other side treated with composition not comprising any PEG 45M and dimethicone (non-inventive composition) is evaluated to have significantly less softness than the side treated with inventive composition. In addition, the stylability and volume of the hair is judged to be better in 60% of the case for inventive composition and in the remaining cases no difference is found.

EXAMPLE 4

According to the Invention

| Phase A | |
| --- | --- |
| Ceteareth-20 | 10.00% |
| Trilaureth-4 Phosphate | 10.00% |
| Steareth-2 | 3.00% |

-continued

| | |
|---|---|
| Mineral Oil | 14.00% |
| Dimethicone/Dimethiconol mixture* | 2.00% |
| Phase B | |
| Aqua | add 100% |
| Propylene Glycol | 5.00% |
| PEG-45M | 0.4% |
| DMDM Hydantoin | 0.2% |
| Phase C) | |
| Parfum | 0.30% |

*commercially available raw material DC 1503 form Dow Corning

The composition is prepared in the same way as in the example 1. The preparation so obtained has a viscosity of 610.000 mPa·s measured as given in the description.

Similar results are obtained as in examples 1 and 2 (non inventive), and 3, when composition according to Example 4 is compared to a non inventive composition produced either by exclusion of silicone component or by exclusion of high molecolare weight polyethylenegylcole.

EXAMPLE 5

According to the Invention

| | |
|---|---|
| Phase A | |
| Ceteareth-20 | 10.00% |
| Ceramide of the formula** | 0.20% |
| Trilaureth-4 Phosphate | 10.00% |
| Steareth-2 | 3.00% |
| Mineral Oil | 14.00% |
| Dimethicone/Dimethiconol mixture* | 2.00% |
| Phase B | |
| Aqua | add 100% |
| Propylene Glycol | 5.0% |
| PEG-45M | 0.4% |
| DMDM Hydantoin | 0.2% |
| Phase C) | |
| Parfum | 0.30% |

*commercially available raw material DC 1503 form Dow Corning.
**as given in the description $R_{14}$ is $C_{15}H_{31}$; $R_{15}$ is $C_{16}H_{33}$ and $R_{16}$ is $CH_3$ and n = 2

The composition is prepared in the same way as in the example 1. The preparation so obtained has a viscosity of 610.000 mPa·s measured as given in the description.

EXAMPLE 6

According to the Invention

| | |
|---|---|
| Phase A) | |
| Ceteareth-20 | 20.00% |
| PEG-7 Glyceryl cocoate | 10.00% |
| Mineral oil | 15.00% |
| Dimethicone | 2.00% |
| Phase B) | |
| Water | add 100% |
| PVP | 2.00% |
| Glycerin | 15.00% |

| | |
|---|---|
| DMDM hydantoin | 0.20% |
| Propylene glycol | 5.00% |
| PEG-45M | 0.40% |
| Phase C) | |
| Parfum | 0.30% |

EXAMPLE 7

According to the Invention

| | |
|---|---|
| Phase A) | |
| Ceteareth-20 | 20.00% |
| Ceramide of the formula** | 0.20% |
| Oleic acid | 0.50% |
| Avocadin | 0.20% |
| PEG-7 Glyceryl cocoate | 10.00% |
| Mineral oil | 15.00% |
| Dimethicone | 2.00% |
| Phase B) | |
| Water | add 100% |
| PVP | 2.00% |
| Glycerin | 15.00% |
| Benzyloxyethanol | 1.00% |
| DMDM hydantoin | 0.20% |
| Propylene glycol | 5.00% |
| PEG-45M | 0.40% |
| Phase C) | |
| Parfum | 0.30% |

**as given in the description $R_{14}$ is $C_{15}H_{31}$; $R_{15}$ is $C_{16}H_{33}$ and $R_{16}$ is $CH_3$ and n = 2

EXAMPLE 7

According to the Invention

| | |
|---|---|
| Phase A) | |
| Ceteareth-20 | 20.00% |
| Cetrimonium chloride | 1.00% |
| PEG-7 Glyceryl cocoate | 10.00% |
| Mineral oil | 15.00% |
| Dimethicone | 2.00% |
| Phase B) | |
| Water | add 100% |
| PVP | 2.00% |
| Glycerin | 15.00% |
| DMDM hydantoin | 0.20% |
| Propylene glycol | 5.00% |
| PEG-45M | 0.40% |
| Phase C) | |
| Parfum | 0.30% |

The invention claimed is:
1. A leave-in hair conditioning composition in microemulsion form, comprising, in a cosmetically acceptable aqueous medium
   (a) a surfactant as an emulsifier, and
   (b) one or more mineral oil at a concentration of 14% to 35%, and
   (c) one or more silicone oil, and

(d) at least one polyethyleneglycol selected from the group consisting of PEG-20M, PEG-23M, PEG-25M, PEG-45M, PEG-90M, PEG-115M and PEG-160M, and wherein component (b) and component (c) are present in the composition at a weight ratio of about 20:1 to 5:1, and the composition is free of fatty alcohol and has a pH in the range of 5 to less than 8.

2. The hair conditioning composition according to claim 1 wherein the composition comprises emulsifiers at concentration of 0.5 to 35% by weight calculated to total composition.

3. The hair conditioning composition according to claim 1 wherein the composition comprises component (c) at a concentration of 1% to 35% by weight, calculated to total composition.

4. The hair conditioning composition according to claim 1 wherein the composition comprises oil components, represented by sum of components (b) and (c), at a concentration of 15 to 35% by weight, calculated to total composition.

5. The hair conditioning composition according to claim 1 wherein the composition comprises the at least one polyethyleneglycol at a concentration of 0.05% to 2.5% by weight calculated to total composition.

6. The hair conditioning composition according to claim 1 wherein the composition comprises cationic amphiphilic molecules according to the general formula

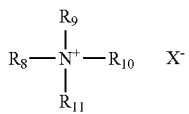

where $R_8$ is a saturated or unsaturated, branched or non-branched alkyl chain with 8-22 carbon atoms or

where $R_{12}$ is saturated or unsaturated, branched or non-branched alkyl chain with 7-21 carbon atoms and n has typical value of 0-4 or

where $R_{13}$ is saturated or unsaturated, branched or non-branched alkyl chain with 7-21 carbon atoms and n has typical value of 0-4, and $R_9$ is a hydrogen, lower alkyl chain with 1 to 4 carbon atoms, saturated or unsaturated, branched or non-branched alkyl chain with 8-22 carbon atoms or

where $R_{12}$ is saturated or unsaturated, branched or non-branched alkyl chain with 7-21 carbon atoms and n has typical value of 0-4 or

where $R_{13}$ is saturated or unsaturated, branched or non-branched alkyl chain with 7-21 carbon atoms and n has typical value of 0-4 and $R_{10}$ and $R_{11}$ are independent from each other H or lower alkyl chain with 1 to 4 carbon atoms, and X is chloride, bromide or methosulfate.

7. The hair conditioning composition according to claim 1 wherein the composition comprises one or more polymers selected from anionic, cationic, nonionic and/or amphoteric ones.

8. The hair conditioning composition according to claim 1 wherein the composition additionally comprises UV filters.

9. The hair conditioning composition according to claim 1 wherein the composition comprises a ceramide compound of the following formula

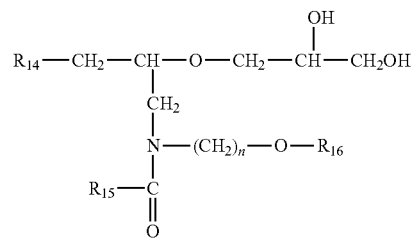

where $R^{14}$ and $R^{15}$ are independent from each other alkyl- or, alkenyl group with 10 to 22 carbon atoms, $R^{16}$ is methyl, ethyl, n-propyl or isopropyl group and n is a number between 1 to 6.

10. The hair conditioning composition according to claim 1 wherein the composition comprises fatty acids with 10 to 24 carbon atoms.

11. The hair conditioning composition according to claim 1 wherein the composition comprises phytosterol.

12. The hair conditioning composition according to claim 1 wherein it has a viscosity of at least 100,000 mPa·s measured at 20° C. with a Brookfield viscosimeter with Spindle F from Helipath Spindle Set at 10 rpm.

13. A method for treating hair comprising:
improving hair shine and softness of the hair by applying the hair conditioning composition according to claim 1 to the hair.

14. The hair conditioning composition according to claim 1 wherein the surfactant is trilaureth-4-phosphate.

15. The hair conditioning composition according to claim 1 wherein the surfactant is Ceteareth-20.

16. The hair conditioning composition according to claim 1, consisting essentially of
a. an anionic surfactant as an emulsifier, and
b. one or more mineral oil at a concentration of 14% to 35%, and
c. one or more silicone oil, and
d. at least one polyethyleneglycol selected from the group consisting of PEG-20M, PEG-23M, PEG-25M, PEG-45M, PEG-90M, PEG-115M and PEG-160M, and
e. a nonionic surfactant as an emulsifier,
wherein anionic and nonionic surfactants are present in the composition at a weight ratio of 10:1 to 1:3 and the mineral oil and silicone oil are present in the composition at a weight ratio of 20:1 to 1:1.

17. The hair conditioning composition according to claim 1, wherein the surfactant is anionic surfactant in the range of 0.5-10.0 wt %.

18. The hair conditioning composition according to claim 1, wherein component (c) is present in the composition at a concentration of at least 13 wt %.

* * * * *